United States Patent [19]

Novak et al.

[11] Patent Number: 4,634,506
[45] Date of Patent: Jan. 6, 1987

[54] PROCESS FOR PREPARING OLEFIN OXIDES

[75] Inventors: Leo R. Novak; Dennis J. Milligan, both of Lake Jackson, Tex.

[73] Assignee: The Dow Chemical Company, Midland, Mich.

[21] Appl. No.: 764,683

[22] Filed: Aug. 12, 1985

[51] Int. Cl.$^4$ ............................................. C25B 3/02
[52] U.S. Cl. ................................................. 204/80
[58] Field of Search ................................. 204/74, 80

[56] References Cited

U.S. PATENT DOCUMENTS

| | | | |
|---|---|---|---|
| 3,147,203 | 9/1964 | Klass | 204/80 |
| 3,288,692 | 11/1966 | Leduc | 204/80 |
| 3,394,059 | 7/1968 | Young | 204/78 |
| 3,427,235 | 2/1969 | LeDuc | 204/78 |
| 3,635,803 | 1/1972 | Binns et al. | 204/80 |

FOREIGN PATENT DOCUMENTS 1176649 12/1966 United Kingdom .
136176 9/1983 United Kingdom ................. 204/79

OTHER PUBLICATIONS

T. Bejeramo et al., *The Electrochemical Production of Propylene Oxide in a Small Pilot Plant*, 58 Trans, I. Chem. E. 28-32 (1980).

J. A. Kent, *Riegel's Handbook of Industrial Chemistry*, 779-780, 795-796 (1974).

*Primary Examiner*—R. L. Andrews
*Attorney, Agent, or Firm*—J. G. Carter

[57] ABSTRACT

An olefin oxide is produced from an olefin in an electrolytic cell by mixing an aqueous electrolyte and liquid olefin under pressure, flowing the liquid mixture through a restricting device into the electrolytic bath of the cell to reduce the pressure of the mixture and to vaporize the olefin, and applying an electric current to the electrolyte/olefin mixture. The electrolyte includes a metal halide, a carbonate salt and a bicarbonate salt.

23 Claims, 2 Drawing Figures

PROCESS FOR PREPARING OLEFIN OXIDES

TECHNICAL FIELD

The present invention relates to the preparation of olefin oxides from olefins. More particularly, the present invention relates to the preparation of olefin oxides from olefins through electrolysis.

BACKGROUND OF THE INVENTION

Olefin oxides constitute a valuable group of organic chemicals which are useful for the preparation of other chemical and industrial products. Propylene oxide, for example, is used in the preparation of propylene and polypropylene glycols. The major uses of propylene glycol are in resins, cellophane, hydraulic fluids, tobacco humectant and cosmetics. Polypropylene glycols are used in the production of polyurethanes. Other uses of propylene oxide are in isopropanolamines, glycol ethers for hydraulic fluids, surfactants and demulsifiers.

A well known process for the production of olefin oxides is the conventional chlorohydrin process. In that process, olefin, chlorine and water are mixed in a reaction vessel. The water and the chlorine form hypochlorous acid that reacts rapidly with the olefin to form chlorohydrin. Following the chlorohydrin reacts with slaked lime to form the corresponding olefin oxide. Conventional chlorohydrin processes for the production of ethylene and propylene oxides are described in J. A. Kent, *Riegel's Handbook of Industrial Chemistry* 779-80, 795-96 (1974). The conventional chlorohydrin process generates large amounts of undesirable by-products such as olefin dichlorides and olefin glycols.

Other well known processes for the production of olefin oxides are electrolytic chlorohydrin processes. Several electrolytic chlorohydrin processes that have been used in the past are described in U.S. Pat. Nos. 3,288,692, 3,394,059, 3,427,235, 3,635,803; German Pat. No. 1,176,649; and, T. Bejerano et al. *The Electrochemical Production of Propylene Oxide in a Small Pilot Plant*, 58 Trans. I. Chem. E. 28-32 (1980).

U.S. Pat. No. 3,288,692 discloses a process which comprises electrolysing an aqueous medium having a metal halide electrolyte while introducing an olefin to the vicinity of the anode of the electrolyte reaction zone to produce olefin oxide. The cell utilized may be of the diaphragm or diaphragmless type. The electrolyte and the olefin flow to the cell via two different lines.

U.S. Pat. No. 3,394,059 discloses a process for electrolytically oxidizing olefin to olefin oxides in a diaphragmless cell in the presence of an aqueous electrolyte which contains an acqueous bromide salt. According to the process disclosure, carbonate salt could be added to the electrolyte to increase its electrical conductivity. Olefin is introduced as vapor into the electrolyte that is already present in the cell.

U.S. Pat. No. 3,427,235 discloses a process of electrolytically oxidizing an olefin to an olefin oxide in an aqueous electrolyte. Oxygen that is generated at the oxide surface of the cell reacts with the olefin to produce the olefin oxide.

U.S. Pat. No. 3,635,803 discloses a process for producing an olefin oxide by mixing an olefin with an electrolyte containing an acetate and by subjecting the mixture to electrolysis. Vapor olefin is introduced into the electrolyte in the cell via a glass frit to form olefin bubbles in the electrolyte.

United Kingdon Patent Specification No. 1,176,649 discloses an electrolytc process for producing olefin oxides from olefins by using among other things an aqueous electrolyte containing a metal halide. The process is carried out in a cell having a diaphragm made out of thermoplastic material.

One disadvantage of the previous processes is that the methods of mixing the olefin and the electrolyte are inadequate whereby the processes have been ineffecient due to poor mixing. Another disadvantage of those processes is that they form a large amount of undesirable by-products including olefin dihalides and olefin glycols.

The present invention discloses a new process that provides better mixing between the electrolyte and the olefin, increases the surface area between the electrolyte and the olefin and reduces the formation of undesirable by-products. These and other advantages of the present invention will become apparent from the following description.

SUMMARY OF THE INVENTION

Olefin oxide is manufactured in an electrolytic cell by contacting an olefin with an aqueous electrolyte. Liquid olefin is combined with the liquid electrolyte, before they enter the cell, at a pressure in which the olefin remains liquid. The pressure of the mixture is reduced to a pressure in which the olefin vaporizes by passing the mixture through an orifice being submerged in the electrolytic bath of the cell. The mixture exiting the orifice and entering the bath comprises a vapor/liquid mixture wherein small olefin bubbles are uniformly suspended in the liquid electrolyte. The aqueous electrolyte contains a metal halide and a carbonate salt, and preferably, a bicarbonate salt.

BRIEF DESCRIPTION OF THE DRAWINGS

For in detail description of the invention, reference will now be made to the accompanying drawings, wherein.

DETAILED DESCRIPTION OF THE INVENTION

Figure 1:
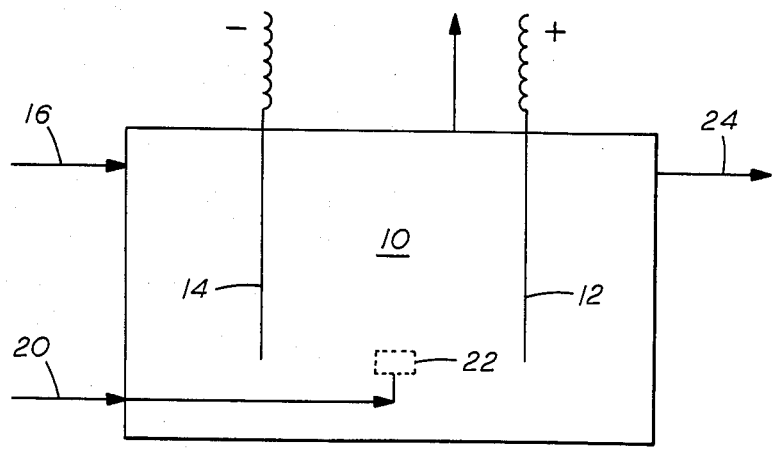
FIG. 1 illustrates diagramatically one embodiment of the invention.

According to the present invention an olefin is electrolytically oxidized in an electrolytic cell by contacting the olefin with an aqueous electrolyte. The olefin and the electrolyte are thoroughly mixed before they flow into the electrolytic cell by combining the olefin in a liquid state and the electrolyte at a pressure that is sufficient to maintain the mixture in the liquid state, and flowing the mixture into the electrolytic bath of the cell through an orifice that is submerged in the bath to reduce its pressure to a pressure at which the olefin is vaporized.

In practicing the invention, a conventional electrolytic cell is provided with an anode and a cathode. Any anode and cathode made out of suitable material having good electrical conductivity may be used, including a ruthenium-coated anode and a titanium cathode. The anode and cathode are electrically connected to a positive and negative side of a direct current source, respectively. A suitable electric potential is applied across the positive and negative sides of the current source that is sufficient to promote the electrolytic reactions of the present invention.

While the current density and electric potential across the electrical source may vary, the current density and electric potential used in practicing this invention should be appropriate to promote the desired reactions and to prohibit the undesired ones. The magnitudes of current densities and electric potentials may range from 0.25 to 1.4 Amps/in$^2$ and 1.85 to 3.50 Volts.

The numerous improvements achieved by the invention, including better mixing and higher efficiency, are more necessary in cells that do not have a diaphragm separating the anode from the cathode compartment. Therefore, it is preferred to practice the invention in a diaphragmless cell. It should be understood, however, that the present invention could also be practiced with a cell having a diaphragm separating the anode from the cathode compartment and that the benefits arising out of the invention would also be achieved in such cells.

Although the invention may be carried out in a batch mode, it is preferred that it is carried out in a continuous mode. Accordingly, aqueous electrolyte and olefin flow continuously into the electrolytic cell where they are subjected to the electrolytic effect to produce hydrogen gas, olefin oxide and certain byproducts. Vapor product comprising hydrogen, olefin oxide and unreacted olefin escape from the liquid medium and is collected downstream from the electrolytic cell. The vapor product is separated by conventional means to obtain substantially pure hydrogen, olefin oxide, and olefin. The hydrogen and olefin oxide products may be sold or utilized for many purposes independent of this operation. The recovered olefin, however, may be recycled to the electrolytic cell for use in the process.

Electrolyte containing dissolved olefin oxide, olefin and by-products of the reaction occurring therein is continuously removed from the cell while being replaced by the electrolyte entering such cell with the olefn. The dissolved olefn oxide, olefin and by-products are removed from the contaminated electrolyte downstream by conventional methods.

Good mixing between the aqueous electrolyte and the olefin as well as a large surface area between the olefin and the electrolyte are necessary to achieve a high olefin conversion and a high olefin oxide yield. The present invention discloses a method that improves the mixing of the electrolyte and the olefin and that increases the surface area therebetween. Accordingly, before entering the cell, the olefin being in its liquid state is combined with the aqueous electrolyte at a pressure that is at a level that is sufficient to maintain the entire mixture in the liquid state. Following, the mixture flows into the cell via a conventional tube that is submerged in the liquid bath in the electrolytic cell. The submerged end of the tube is restricted by a restricting device such as an orifice that is constructed out of strong material such as steel capable of withstanding the large upstream pressure. As the liquid mixture flows through the orifice, its pressure is reduced to the pressure of the cell which is maintained at a level at which the olefin is vaporized. The flow of the mixture through the orifice, the drop in the pressure thereof and the vaporization of the olefin cause the formation of a vapor/liquid mixture in which very small bubbles of olefin vapor are uniformly suspended in the electrolyte, whereby good mixing as well as a large vapor/liquid contact surface area are achieved between the olefin and the electrolyte. Furthermore, the flow of the mixture through the orifice and the simultaneous large drop in the pressure thereof result in the increase of the velocity of the mixture entering the liquid bath of the cell and in the creation of a turbulent region, whereby the uniformity of the vapor/liquid mixture is enhanced.

It should be understood that the method of introducing the electrolyte and the olefin into the cell discussed hereinabove would be effective as long as the pressure and the temperature of the olefin/electrolyte mixture before it flows through the orifice is at a level at which the entire mixture remains in the liquid state and as long as the pressure and the temperature of the mixture exiting the mixture is at a level at which substantially all the olefin is vaporized. It should be understood, however, that the benefits arising out of the method increase as the difference between the pressure of the mixture upstream the orifice and the pressure downstream thereof increases. Consequently, a large pressure drop in the orifice is preferred over a small one.

The pressure drop through the orifice, the size of the orifice and the flowrates of the electrolyte and the olefin would vary from case to case in accordance with capacity requirements, the reactant olefin and the temperature conditions of the system. In the production of propylene oxide from propylene, for example, the flowrate of the electrolyte may range from 50 to 200 ml/min/700 ml cell volume, the flowrate of the liquid propylene may range from 0.5 to 2 ml/min/700 ml cell volume and the pressure drop may range from 50 to 450 psi when the propylene is available at ambient temperature.

As regards the pressure and temperature conditions of the electrolytic cell, the pressure/temperature combination should be such that the electrolyte is in the liquid state and substantially all of the olefin is in the vapor state. In general, the invention may be conveniently practiced at a temperature near room temperature and at a pressure that is close to atmospheric.

The aqueous electrolyte contains a metal halide compound. It is preferred, however, to utilize a metal bromide compound such as potassium bromide to minimize the undesirable halogenation of the olefin that occurs when halides other than bromides are used. It should be understood, however, that any halide compound that is at least partially soluble in the water could be used to practice the invention. As regards the amount of the halide that should be used in the electrolyte, such amount varies depending on the halide compound used. It has been observed, however, that when potassium bromide is used a concentration of about 1% by weight of potassium bromide in the aqueous electrolyte is preferred in carrying out this reaction.

In accordance with the invention, a carbonate salt is added to the electrolyte to improve said electrolyte. Although any carbonate salt may be utilized for that purpose, it is preferred that an alkali metal carbonate salt, such as potassium carbonate, be added to the electrolyte in an amount that may range from 5 to 45 percent by weight at temperatures ranging from 5° to 40° C. The addition of the carbonate salt causes several beneficial results that are more pronounced as the amount of the carbonate salt increases. More particularly, the addition of the carbonate salt increases the electrical conductivity of the electrolyte whereby the cell voltage required to carry out the reaction and the energy consumption is decreased. Furthermore, the presence of salt ions hinders the formation of side products by tying up the ions that react to form such side products, thereby increasing the olefin oxide yield. Furthermore, the addition of carbonate salt to the electrolyte decreases the solubility of the olefin and the olefin oxide in such electrolyte whereby the amount of olefin oxide and unreacted olefin solubilized in the electrolyte exiting the cell is reduced and the olefin oxide and olefin recovery efficiency is improved.

In accordance with the invention, a bicarbonate salt is also added to the electrolyte to improve said electrolyte. Although any bicarbonate salt may be utilized for that purpose, it is preferred that an alkali metal bicarbonate salt, such as sodium bicarbonate, be added to the electrolyte in an amount that may range from 1 to 10 percent by weight. The addition of the bicarbonate salt reduces the side product formation and increases the olefin oxide yield.

The present invention may be utilized for the production of a wide range of olefin oxides having from two to more than nine carbon atoms. It is, however, preferred to utilize the invention for the production of olefin oxides in the lower carbon atom number range such as ethylene, propylene and butylene.

The following examples further illustrate the invention but are not to be construed as limitations on the scope of the process contemplated herein.

EXAMPLE 1

Referring now to FIG. 1, a general electrolyte mini-cell 10 applicable to the manufacturing of chlorine was used to produce propylene oxide. The cell was fitted with a ruthenium coated anode 12 and a titanium cathode 14. The anode and cathode compartments were not separated by a diaphragm. Aqueous electrolyte containing one percent (1%) potassium bromide by weight and the balance deionized water was continuously pumped through line 16 into electrolytic cell 10 maintained at atmospheric pressure and at room temperature. The residence time of the electrolyte was sixty minutes. Vapor propylene was added as a gas to cell 10 via line 20 through a glass frit 22 where it was mixed with the electrolyte. The electric potential across cell 10 was 4.2 Volts and the current density was 0.326 Amps/in$^2$. The propylene reacted with the electrolyte to produce hydrogen, propylene oxide and other by-products. Electrolyte overflowing from the cell was taken via line 24 to a stripping column where the propylene oxide and the propylene were removed from the electrolyte. The electrolyte was then returned to the cell. The propylene conversion was 5 percent. The yields of propylene oxide, propylene dibromide and propylene glycol were 89.6, 1.3 and 9.1 percent, respectively. Table A includes a tabulation of the operating parameters used in Example 1 together with the pertinent operating results for comparison with the corresponding parameters and results of Example 2.

EXAMPLE 2

Figure 2:
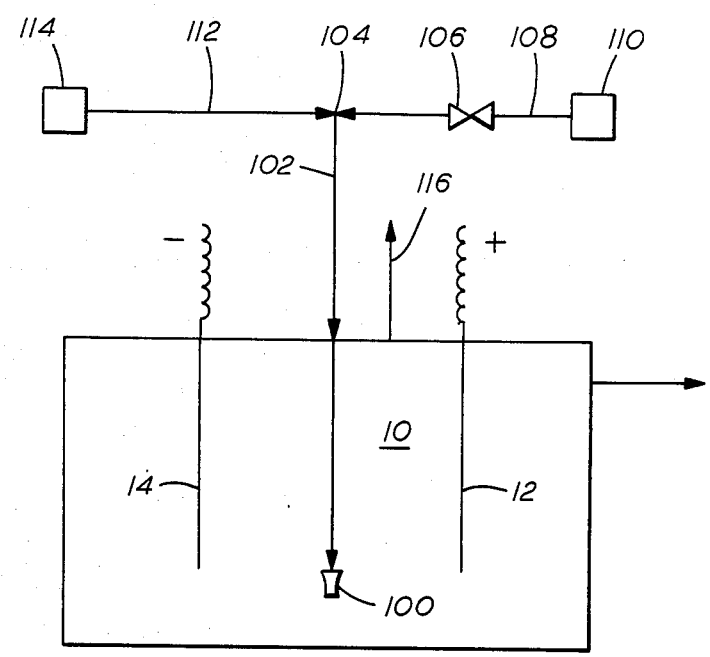
FIG. 2 illustrates diagramatically another embodiment of the invention incorporating modifications to the embodiment illustrated in FIG. 1.

Referring now to FIG. 2, the electrolytic cell used in Example 1 was utilized with a different configuration for introducing the electrolyte and the propylene in the cell. More particularly, a 0.017 cm orifice 100 made out of stainless steel was fitted on the end of a ¼" monel tubing 102. The orifice end of the tubing was fitted inside cell 10 so that it would be submerged in the electrolytic bath. The other end was fitted with a connector tee. One end of the tee 104 was connected to a ¼" stainless steel tubing 106 having a control valve 108 and being connected to a source 110 of liquid propylene. The other end of tee 104 was connected to a ¼" monel tubing 112 being connected to a source 114 of electrolyte. Electrolyte having the same composition as the electrolyte used in Example 1 was pumped into tee 104 at a pressure of approximately 200 psig where it was mixed with liquid propylene available at approximately the same pressure and at ambient temperature from the liquid propylene source. The amount of propylene was controlled by control valve 108 of the propylene line to an amount of about 1 to 2 ml/min. The combined liquid mixture flowed through orifice 100 into cell 10 that was maintained at atmospheric pressure and at room temperature. The pressure drop through orifice 100 caused the propylene to vaporize and to form with the electrolyte a vapor/liquid mixture in which small vapor propylene bubbles were uniformly suspended in the liquid electrolyte. The propylene reacted with the electrolyte to produce hydrogen and propylene oxide exiting cell 10 and via line 116. Overflowing electrolyte was taken to a stripping column via line 118 where the dissolved propylene oxide and propylene were removed from the electrolyte. The electric potential across the cell was 4.2 Volts and the current density was 0.326 Amps/in$^2$. The residence time of the electrolyte was seven minutes. The conversion of the propylene was 10 percent. The yields of the propylene oxide, propylene dibromide and propylene glycol were 90, 10 and less than 0.1 percent, respectively. Table A includes a tabulation of the operating parameters and the operating results of Example 2 for comparison with the corresponding parameters and results of Example 1.

TABLE A

| Comparisons Between Examples 1 and 2 | | |
|---|---|---|
|  | Example 1 | Example 2 |
| Electric Potential, Volts | 4.2 | 4.2 |
| Current Density, Amps/In$^2$ | 0.326 | 0.326 |
| Residence Time of Electrolyte, Minutes | 60 | 7 |
| Propylene Conversion, Percent | 5 | 10 |
| Propylene Oxide Yield, Percent | 89.6 | 90 |
| Propylene Dibromide Yield, Percent | 1.3 | 10 |
| Propylene Glycol Yield, Percent | 9.1 | 0.1 |

EXAMPLE 3

The electrolytic cell together with the propylene/electrolyte injection apparatus used in Example 2 was utilized. Electrolyte containing one percent (1%) potassium bromide by weight and the balance deionized water was mixed in the tee with liquid propylene at about 200 psig. The combined mixture flowed through the orifice into the electrolyte that was maintained at atmospheric pressure and at a temperature of about 30° C. Overflowing electrolyte was taken to a stripping column where propylene oxide and propylene were removed from the electrolyte. The residence time of the electrolyte was 7 minutes and the flow rate of the liquid propylene was 1 to 2 ml/min at 200 psig. The electric potential was 4.1 Volts and the current density was 0.326 Amps/in$^2$. The propylene conversion was six percent and the propylene oxide yield was 88 percent. Table B includes a tabulation of the operating parameters and results of Example 3 for comparison with Examples 4 and 5.

EXAMPLE 4

The procedure of Example 3 was repeated with the exception that ten percent potassium carbonate by weight replaced an equivalent amount of deionized water in the electrolyte. As a result, the electric potential was reduced to 2.4 Volts while the current density was maintained to 0.326 Amps/in$^2$, the propylene conversion was increased to 12 percent and the propylene oxide yield was increased to 92 percent. Table B includes the operating parameters and results of Example 4 for comparison with Examples 3 and 5.

EXAMPLE 5

The procedure of Example 4 was repeated with the exception that the amount of potassium carbonate was increased to forty percent by weight. As a result, the electric potential was reduced to 2.2 Volts while the current density was maintained at 0.326 Amps/in$^2$, the propylene conversion was increased to 14 percent and the propylene oxide yield was increased to 94 percent. Table B includes the operating parameters and results of Example 5 for comparison with Examples 3 and 4.

TABLE B

Comparison Between Examples 3, 4 and 5

|  | Example 3 | Example 4 | Example 5 |
|---|---|---|---|
| Electrolyte Composition, Wt % | 1% KBr, 99% H$_2$O | 1% KBr, 10% K$_2$CO$_3$, 89% H$_2$O | 1% KBr, 40% K$_2$CO$_3$ 59% H$_2$O |
| Electric Potential, Volts | 4.1 | 2.4 | 2.2 |
| Current Density, Amps/in$^2$ | 0.326 | 0.326 | 0.326 |
| Residence Time of Electrolyte, Minutes | 7–10 | 7–10 | 7–10 |
| Propylene Conversion, Percent | 6 | 12 | 14 |
| Propylene Oxide Yield, Percent | 88 | 92 | 94 |

EXAMPLE 6

The procedure of Example 4 was repeated and the amount of byproducts was measured. Propylene glycol and propylene dibromide yield of one and seven percent, respectively, were measured. The operating parameters and operating results are tabulated in Table C for comparison with the parameters and results of Example 7.

EXAMPLE 7

The procedure of Example 6 was repeated except that one percent of sodium bicarbonate by weight replaced an equivalent amount of deionized water. As a result, the electric potential was reduced to 2.38 Volts while the current density was maintained at 0.326 Amps/in$^2$, the propylene oxide was increased to 95 percent, and the byproduct yield was decreased. Table C includes a tabulation of the operating parameters and results of Example 7 for comparison with the parameters and results of Example 6.

TABLE C

Comparison Between Examples 6 and 7

|  | Example 6 | Example 7 |
|---|---|---|
| Electrolyte Composition | 1% KBr, 10% K$_2$CO$_3$, 89% H$_2$O | 1% KBr, 10% K$_2$CO$_3$, 1% NaHCO$_3$, 88% H$_2$O |
| Electric Potential, Volts | 2.4 | 2.35 |
| Current Density Amps/in$^2$ | 0.326 | 0.326 |
| Residence Time of Electrolyte, Minutes | 7–10 | 7–10 |
| Propylene Conversion, Percent | 12 | 12 |
| Propylene Oxide Yield, Percent | 92 | 95 |
| Propylene Dibromide Yield, Percent | 7 | 3 |
| Propylene Glycol Yield, Percent | 1 | 2 |
| Temperature of Cell, °C. | 30 | 30 |

Although the invention is described with respect to specific embodiments and modifications, the details hereof are not to be construed as limitations except to the extent indicated in the following claims.

What is claimed is:

1. A process for preparing an olefin oxide in an electrolytic cell, comprising:
    mixing aqueous electrolyte with an olefin at a pressure and temperature at which substantially all the olefin is in the liquid state;
    reducing the pressure of the mixture to a pressure at which substantially all the olefin is vaporized;
    flowing the mixture into the cell; and
    effecting an electric current through the electrolyte.
2. The process according to claim 1 further including the step of separating the olefin oxide from the effluent gas.
3. The process according to claim 1 wherein the step of reducing the pressure of the mixture includes the step of passing the mixture through an orifice.
4. The process according to claim 3 wherein said orifice is submerged in a liquid bath in the cell.
5. The process according to claim 1 wherein the electrolyte contains metal halide.
6. The process according to claim 1 wherein said electrolyte includes a carbonate salt.
7. The process according to claim 6 wherein said carbonate salt is potassium carbonate.
8. The process according to claim 6 wherein said electrolyte further includes a bicarbonate salt.
9. The process according to claim 8 wherein said bicarbonate salt is sodium bicarbonate.
10. The process according to claim 1 wherein the step of mixing the aqueous electrolyte with the olefin is carried out at a pressure that is higher than the vapor pressure of the olefin at the mixing temperature.
11. The process according to claim 1 wherein the step of reducing the pressure of the mixture reduces the pressure of the mixture to a pressure that is lower than the vapor pressure of the olefin at the temperature of the mixture.
12. The process according to claim 1 wherein the electrolyte is substantially all in the liquid state.
13. The process according to claim 1 wherein the olefin is ethylene.
14. The process according to claim 1 wherein the olefin is propylene.
15. The process according to claim 1 wherein the olefin is butylene.
16. A process for preparing an olfin oxide in an electrolytic cell, comprising:

mixing an aqueous electrolyte containing a carbonate salt and a bicarbonate salt with an olefin; and effecting an electric current through the electrolyte.

17. The process according to claim 16 wherein the electrolyte includes a metal halide.

18. The process according to claim 17 wherein the carbonate salt is potassium carbonate.

19. The process according to claim 18 wherein the bicarbonate salt is sodium bicarbonate.

20. The process according to claim 16 wherein the olefin is propylene.

21. The process according to claim 16 wherein the olefin is ethylene.

22. The process according to claim 16 wherein the olefin is butylene.

23. The process according to claim 16 further including the step of separating the olefin oxide from the effluent gas.

* * * * *